United States Patent [19]

Dessertine

[11] Patent Number: 5,020,527
[45] Date of Patent: Jun. 4, 1991

[54] INHALER DEVICE WITH COUNTER/TIMER MEANS

[75] Inventor: Pauline L. Dessertine, Flemington, N.J.

[73] Assignee: Texax-Glynn Corporation, Flemington, N.J.

[21] Appl. No.: 482,155

[22] Filed: Feb. 20, 1990

[51] Int. Cl.$^5$ ............................................. A62B 7/00
[52] U.S. Cl. .......................... 128/200.23; 128/200.14; 128/205.23
[58] Field of Search ...................... 128/200.14, 200.23, 128/205.23

[56] References Cited

U.S. PATENT DOCUMENTS

| | | | |
|---|---|---|---|
| 3,183,907 | 3/1965 | Bush et al. | 128/200.23 |
| 3,361,306 | 1/1968 | Grim | 128/200.23 |
| 3,506,004 | 4/1970 | Mann et al. | 128/200.23 |
| 4,291,688 | 9/1981 | Kistler | 128/200.23 |
| 4,484,577 | 11/1984 | Sackner et al. | 128/200.23 |
| 4,677,975 | 7/1987 | Edgar et al. | 128/200.14 |
| 4,817,822 | 4/1989 | Rand et al. | 128/200.23 |

Primary Examiner—Edgar S. Burr
Assistant Examiner—Lisa E. Malvaso
Attorney, Agent, or Firm—Kenneth P. Glynn

[57] ABSTRACT

The present invention is directed to a device for inhaling medicine from an inhalation canister with a spray stem. It includes a hollow-bodied tubular main body having a back end adapted to receive an inhalation canister and a front end adapted for placement to or in a mouth, as well as a spray-directing element fixedly located within the main body, a counter and a timer. The spray-directing element has a continuous opening with an insert end for receiving a spray stem of an inhalation canister and a spray end for directing sprays of medicine through and out of the front end of the main body when an inhalation canister is activated by a user. The counter is connected to the main body for displaying a count of total activations of an inhalation canister and is advanced by each activation of an inhalation canister. The timer keeps track of time between inhalations for the user. Both the counter and the timer are resettable and are preferably electronic and may be contained in a single unit.

10 Claims, 1 Drawing Sheet

INHALER DEVICE WITH COUNTER/TIMER MEANS

BACKGROUND OF THE INVENTION

1. Field of the Invention

The present invention is directed to inhalers for the controlled inhalation of medication by a patient by self-activation. More particularly, it is directed to an inhaler which receives inhalation canisters for manual release of pressurized medication in spray form into the mouth and the inhaler is adapted to include counting and timing capabilities to enhance proper self-administration of doses by patient.

2. Prior Art Statement

The use of inhalers is well known and the art has developed over the past twenty years to cover many versions of the basic concept of a "pumping" type medication applicator. The device is not truly pumped although a pumping like cycle is utilized. The medication is repeatedly released from a disposable canister, e.g. by depressions by the patient to create repeated sprays or inhalations as needed.

U.S. Pat. No. 3,361,306 to W. M. Grim illustrates a typical inhaler where a canister of medication is inserted into the back end of a device and the spray nozzle of the canister sits in a spray-directing member to shoot spray out of the front (mouth) end of the device when the canister is pressed down by a user.

U.S. Pat. No. 3,183,907 describes an inhaler in which a button on its underside is pushed by the user to release a controlled or metered amount of spray from a medication canister held in the top or back end of the inhaler.

U.S. Pat. No 4,817,822 to Paul Rand et al describes an inhaler device which includes counting means for indicating the relative emptiness of a container or the number of doses dispensed. However, this inhaler counting mechanism is attached to the medicine container as well as the inhaler, such as by a retaining ring or retaining cap and is preferably not removed from the container.

Notwithstanding the prior art, the use of counters for an exact count of sprays per application, e.g. five sprays or six sprays each time the device is used, is not taught nor rendered obvious by the prior art, nor is the use of a timer to enable the user to control the elapsed time, e.g. 60 seconds, between each spray of a multispray application, as in the present invention.

SUMMARY OF THE INVENTION

The present invention is directed to a device for inhaling medicine from an inhalation canister with a spray stem. It includes a hollow-bodied tubular main body having a back end adapted to receive an inhalation canister and a front end adapted for placement to or in a mouth, as well as a spray-directing element fixedly located within the main body, a counter and a timer. The spray-directing element has a continuous opening with an insert end for receiving a spray stem of an inhalation canister and a spray end for directing sprays of medicine through and out of the front end of the main body when an inhalation canister is activated by a user. The counter is connected to the main body for displaying a count of total activations of an inhalation canister and is advanced by each activation of an inhalation canister. The timer keeps track of time between inhalations for the user. Both the counter and the timer are resettable and are preferably electronic and may be contained in a single unit.

BRIEF DESCRIPTION OF THE DRAWINGS

The present invention is more fully understood when this specification is taken in conjunction with the drawings which are appended hereto, and wherein.

DETAILED DESCRIPTION OF THE INVENTION

The sufferer of asthma or other respiratory ailment has frequent need for relief from breathing and other difficulties and the use of hand-held inhalers brings frequent releif. These devices sometimes have moving parts, but all are based on three principles. First, the device receives loaded, disposable canisters of medication which today are pressurized but may alternatively be true pump type dispensers. Second, the inhaler holds the canister while the canister outlet is seated in, directed to or connected to a spray-directing element. Third, the user presses something, either the canister, a button on the inhaler or a combination, to effectuate a required discharge.

While the inhaler has brought relief to many patients, some must take repeated dosages at a given application for a specific number of sprays at specified time intervals. Thus, a patient may need, e.g., seven sprays taken at sixty second intervals. However, when an asthma attack occurs, and inhaler relief is needed or even when periodic medication is taken, it is difficult for the patient to keep track of the number of sprays and/or the elapsed time between each spray.

The present invention is directed to aiding the patient by providing counting means and timing means built into the inhaler itself. It is the use of these additions to the inhaler that enables the patient to effectively and efficiently use the inhaler in many situations, e.g. at home, on the job in a manual labor environment, while driving or holding a baby, etc.

The particular internal mechanism is now within the purview of the artisan and not discussed in detail. In other words, electronic stop watches, timers and counting mechanisms are known and available. It is the particular application to the inhaler that constitutes the critical features herein.

Figure 1:
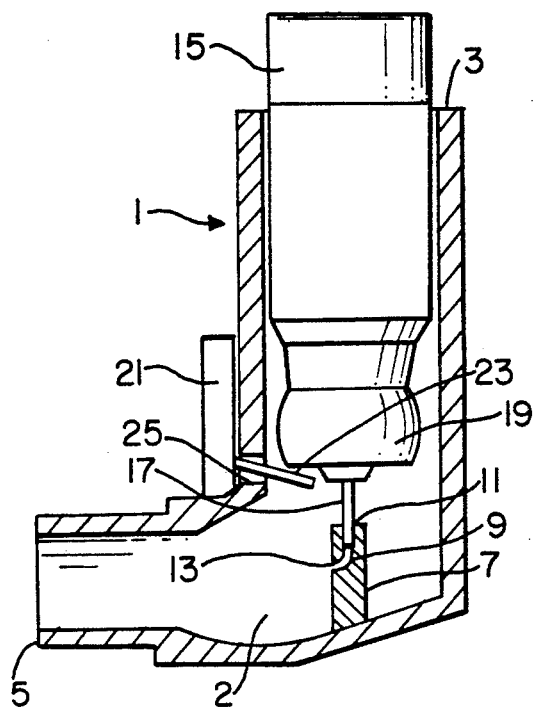
FIG. 1 shows a side cut view of a present invention inhaler with a medication canister inserted therein.

Referring now to FIG. 1, there is shown a side cut view of inhaler 1, having a hollow main body 2, with back end 3 adapted to receive an inhalation canister, and a front end 5 adapted for placement to or in a mouth (although, without exceeding the scope of the invention, it could be for placement relative to the mouth and nostrils or nostrils). Spray-directing element 7 is fixedly located within main body 2, as shown, and includes a continuous opening 9. The opening 9 has an insert end 11 for receiving a spray stem 17 of an inhalation canister 15, and has a spray end 13 for directing sprays or puffs of medicine through and out of the front end 5 of main body 2 when canister 15 is activated by a user.

Figure 2:
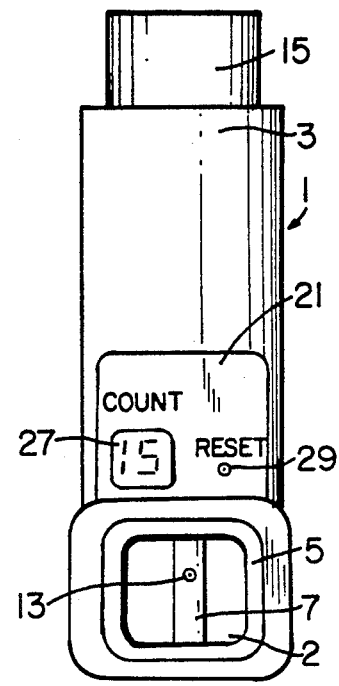
FIG. 2 illustrates a full front view of the device shown in FIG. 1.

Referring now to both FIGS. 1 and 2, like parts are like numbered as FIG. 2 shows a full front view of the inhaler 1 of FIG. 1. Unit 21 includes an automatic counter chip with a long-life miniature battery (not shown) which is activated by downward movement of canister 15 against lever 23, which is connected to unit 21. Lever 23 is located so as to pass through orifice 25 and is movable therein. Each time the user depresses canister 15, lever 23 swings downward and ticks off one more count, which is displayed at LCD 27. Additionally, a timer is activated simultaneously therewith and signals a "beep" sixty seconds after lever 23 is depressed. When a user is finished with the correct number of sprays at, in this case, sixty second intervals, the unit 21 may be simultaneously stopped and reset by depressing reset button 29.

While the device of FIGS. 1 and 2 has an audible signal, it could alternatively be visual or combined audio-visual. Likewise, separate reset buttons and controls for the counter and the timer could be used without exceeding the scope of the present invention. Also, the length of the elapsed time could be preset at an interval different from sixty seconds, and could be programmable, although it is preferred to be preset to simplify its use.

While FIGS. 1 and 2 show an inhaler having no moving parts other than the lever, the present invention could include a pump or a push button or have other features used in available inhalers without exceeding the present invention scope.

Figure 3:
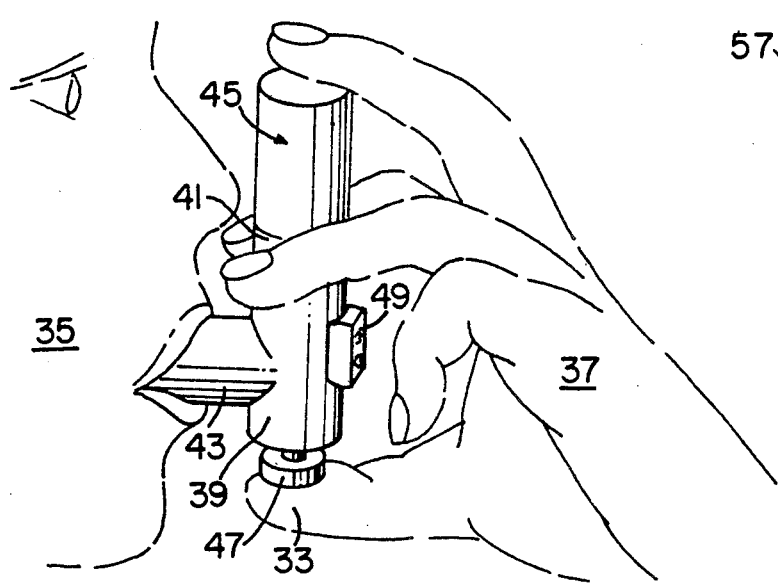
FIG. 3 shows an alternative embodiment present invention inhaler in actual use.

FIG. 3 shows an alternative embodiment of the present invention. User 35 has inhaler 39 in hand 37. In this inhaler 39, push button 47 is depressed to activate canister 45, held firmly in place, and button 47 pushes in a spray stem (not shown) of canister 45 to effectuate a spray. Mouthpiece 43 is inserted as shown with back end 41 receiving canister 45. Combined unit 49 includes dual features and may be activated by lever, button, electrical contact being completed by a metal canister 45, or by any other known mechanism within the purview of the artisan.

Figure 4:
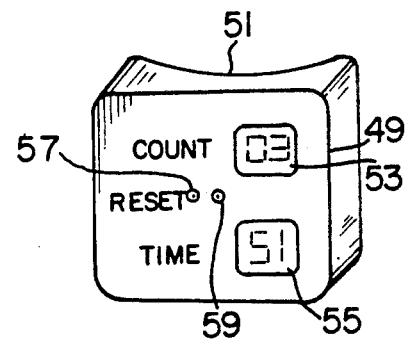
FIG. 4 shows a front oblique view of the counter/timer unit shown on the FIG. 3 inhaler device.

FIG. 4 shows the details of unit 49 of FIG. 3. Unit 49 has a curved back 51 for attachment to inhaler 39 by known plastic-to-plastic means, although the inhaler and/or unit may be metal or metal-plastic and known assembly techniques may be used. Unit 49 includes counter with display 53 and timer with display 55. Reset buttons 57 and 59 are also included.

Since manufacturers today sell or provide inhalers with the medication which are disposable, the present invention inhaler may include a counter/timer unit which is detachable and is usable with many inhalers which are adapted to have the counter/timer unit removably attached thereto. Such embodiments would be included within the scope of the invention. For example the counter/timer unit shown in FIGS. 3 and 4 could be removable with a snap on feature (not shown) or any other known attachment means.

Obviously, numerous modifications and variations of the present invention are possible in light of the above teachings. It is therefore understood that within the scope of the appended claims, the invention may be practiced otherwise than as specifically described herein.

What is claimed is:

1. A device for inhaling medicine from an inhalation canister with a spray stem which comprises:
   (a) a hollow-bodied tubular main body having a back end adapted to receive an inhalation canister and a front end adapted for placement to or in a mouth or nose;
   (b) a spray-directing element fixedly located within said main body, and having a continuous opening with an insert end for receiving a spray stem of an inhalation canister and a spray end for directing sprays of medicine through and out of the front end of said main body when an inhalation canister is activated by a user;
   (c) counting means connected to said main body for displaying a count of total activations of an inhalation canister, said counting means being advanced by each activation of an inhalation canister and being resettable to zero; and,
   (d) timer means connected to said main body for signaling time periods between each activation of an inhalation canister, said timer means including on/off capabilities.

2. The device of claim 1 wherein said counting means is a mechanical counter and is advanceable by contact of an activated inhalation canister with an advancing ratchet or lever connected to said counting means.

3. The device of claim 2 wherein said mechanical counter has a reset button and is spring loaded such that it is resettable to zero by spring activation initiated by depression of said reset button.

4. The device of claim 1 wherein said counting means is electronic and includes a display, a power source and a preprogrammed chip for counting and resetting.

5. The device of claim 4 wherein said counting means is advanceable by contact of an activated inhalation canister with an advancing lever which is connected to said counting means.

6. The device of claim 4 wherein said counting means is advanceable by closing or opening an electric circuit by contact of an activated inhalation canister.

7. The device of claim 1 wherein said counting means is manually advanced by a user.

8. The device of claim 1 wherein said timer means is electronic and includes a display, a power source and a preprogrammed chip for signaling predetermined amounts of time and for resetting.

9. The device of claim 1 wherein said counting means and said timing means are contained in a single electronic unit which includes a display, a power source and a preprogrammed chip for counting, for signaling predetermined amounts of time and for resetting.

10. The device of claim 9 wherein said single electronic unit is removably connected to said main body.

* * * * *